US000001843H

United States Statutory Invention Registration [19]

[11] Reg. Number: H1,843

Bur et al.

[45] Published: Mar. 7, 2000

[54] OPTICAL SENSOR FOR MEASURING FLUORESCENCE ANISOTROPY DURING POLYMER PROCESSING

[76] Inventors: Anthony J. Bur, 623 Muriel St., Rockville, Md. 20852; Steven C. Roth, 8809 Slate Quarry Rd, Dickerson, Md. 20842

[21] Appl. No.: 08/953,288

[22] Filed: Oct. 17, 1997

[51] Int. Cl.[7] ..... F21V 9/16; G01N 21/64; G01N 33/48

[52] U.S. Cl. ..... 250/458.1; 250/459.1; 250/461.1; 250/461.2; 356/41

[58] Field of Search ..... 250/458.1, 459.1, 250/461.1, 461.2; 356/41

[56] References Cited

U.S. PATENT DOCUMENTS

| | | | |
|---|---|---|---|
| 4,521,111 | 6/1985 | Paulson, Jr. et al. . | |
| 4,529,306 | 7/1985 | Kilham et al. . | |
| 4,651,011 | 3/1987 | Ors et al. . | |
| 5,037,763 | 8/1991 | Petisce . | |
| 5,151,748 | 9/1992 | Bur et al. . | |
| 5,369,483 | 11/1994 | Wilson . | |
| 5,384,079 | 1/1995 | Bur et al. . | |
| 5,626,134 | 5/1997 | Zuckerman | 356/41 |

OTHER PUBLICATIONS

"Orientation of Rigid Rods Dissolved in Deformed Networks", B. Erman et al, Polymer 28, 727 (1987).

"A Study of the Orientations of Flourescent Molecules Incorporated in Uniaxially Oriented Poly(ethylene terephthalate) Tapes"; J. H. Nobbs, et al; Polymer 15, 287 (1974).

"A Characterization of Orientation in a Highly Oriented Polymeric Fiber by Fluorescence Depolarization"; L. L. Chapoy et al; Macromolecules 20, 680 (1979).

"Fluorescence Anisotropy Measurements on Polymer Materials as a Function of Applied Shear and Extensional Stress"; A. J. Bur et al; Macromolecules 25, 3503 (1992).

"Fluorescence Anisotropy Measurements on a Polymer Melt as a Function of Applied Shear Street"; A. J. Bur et al, Proc. Ann. Tech. Mtg. Soc. Plastics Eng., May 1992, p. 2088.

*Primary Examiner*—Daniel T. Pihulic

[57] ABSTRACT

An optical sensor containing polarizing optical components measures fluorescence anisotropy of fluorescent dyes. The measurement involves the detection of vertical and horizontal components of fluorescent light. Using Glan-Taylor and Wollaston calcite polarizers, both vertical and horizontal components are collected by separate optical fibers and measured simultaneously using a two-channel photon counter. One application of this sensor is the measurement of molecular orientation during polymer processing. Two sensor head designs are described, one of which fits into the ½ inch instrumentation port in polymer processing machines. To carry out process monitoring, a fluorescent dye is mixed with a polymer resin at approximately 10 ppm by weight concentration. Dyes which have geometrical asymmetry in their molecular structure or are covalently bonded to the polymer molecule are usually used. The anisotropy measurement yields information about the orientation of the dye molecule in an oriented medium. Anisotropy measurements of fluorescent dyes in media other than polymers can also be obtained using this sensor.

16 Claims, 9 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

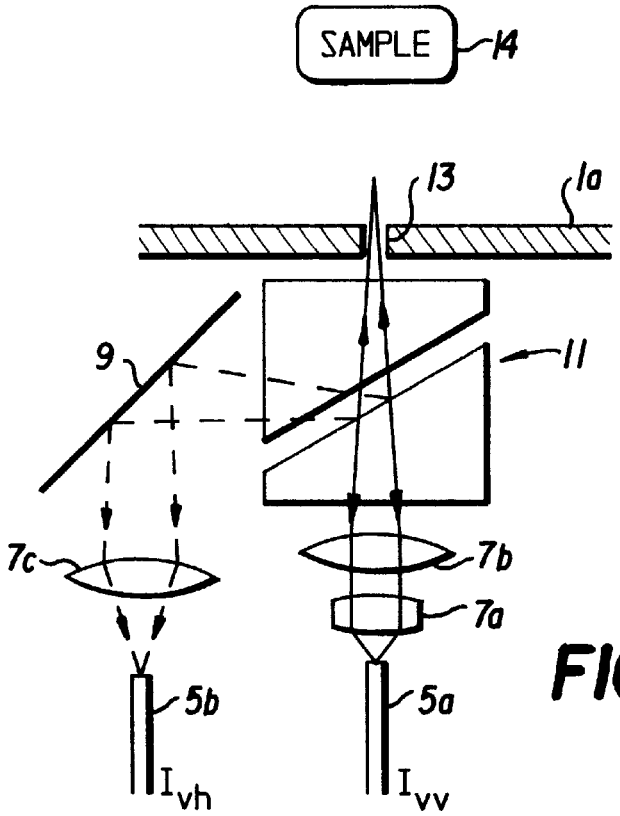
FIG. 3C
FIG. 7
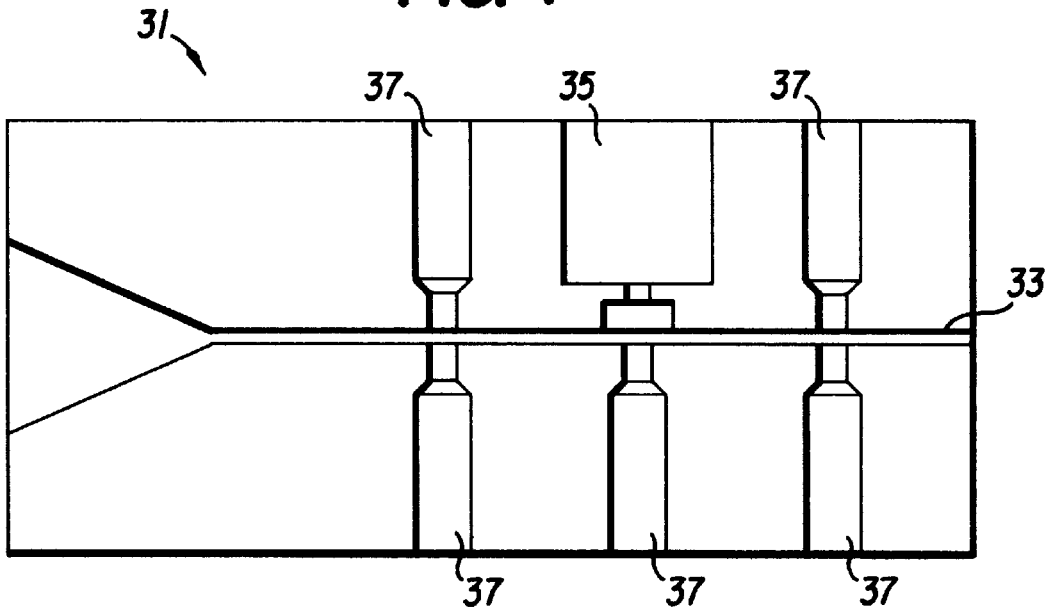

OPTICAL SENSOR FOR MEASURING FLUORESCENCE ANISOTROPY DURING POLYMER PROCESSING

FIELD OF THE INVENTION

The present invention is directed to an optical sensor containing polarizing optical components for measuring fluorescence anisotropy of fluorescent dies.

DESCRIPTION OF RELATED ART

A fundamental property of polymer materials which determines their performance and properties is spatial molecular orientation. During polymer processing, molecular orientation is caused by shear and extensional stresses applied to the material. Optical methods which can be used to measure molecular orientation are birefringence, optical dichroism, and fluorescence anisotropy. The first two methods require that the probing light transmit through the material, but fluorescence measurements can be carried out via excitation and detection from the same surface. Using a one-sided sensor design, it is possible to access regions of processing machines which would other-wise be unaccessible for detecting molecular orientation by optical methods.

Fluorescence anisotropy is used to measure the orientation of a fluorescent molecule. Its application to polymer processing involves the doping of a fluorescent molecule into a resin at very low concentrations, such as 10 ppm by weight. Such low concentrations do not affect the performance of the polymer product. In some cases the polymer molecule contains fluorescent moieties which eliminate the need for adding a fluorescent dye. Also, the fluorescent dye can be covalently bonded or "tagged" to the polymer molecule.

Molecular orientation is usually measured with respect to the resin flow direction in a processing machine. The anisotropy measurement involves the use of polarized excitation light and analysis of the emitted fluorescent light polarization. Fluorescence anisotropy, r, is defined as $$r = \frac{I_{vv} - I_{vh}}{I_{vv} + 2I_{vh}} \tag{1}$$

where $I_{vv}$ and $I_{vh}$ are the vertically and horizontally polarized fluorescent light produced by vertically polarized excitation light.

FIG. 1 shows a coordinate system used to determine these components. In the coordinate system of FIG. 1, the vertical and horizontal directions are the z and x directions, while the direction of light travel is the y direction. The z direction is also the direction of extensional flow of a resin. Thus, $I_{zz}=I_{vv}$, and $I_{zx}=I_{vh}$.

Orientation of a fluorescent molecule is expressed in terms of the orientation of its absorption dipole. Orientation of a vector a is defined by the angles θ and ϕ as depicted in FIG. 2. Molecular models which relate absorption dipole orientation to $I_{vv}$ and $I_{vh}$ are expressed in terms of the average cosines of θ and ϕ. In general, $$r = f\left(\langle\cos^2\theta\rangle, \langle\cos^2\phi\rangle, \frac{\tau_f}{\tau_r}\right) \tag{2}$$

where $\tau_f$ is the fluorescence decay time of a molecule and $\tau_r$ is the rotational relaxation time of the molecule. The term $\tau_f/\tau_r$, appears in the relationship because a molecule with small $\tau_r$ relative to $\tau_f$ tends to randomize its orientation before it has a chance to radiate its fluorescence and thus shows no anisotropy. In other words, over the time scale of observation, the short relaxation time $\tau_r$ allows the molecule to lose its orientation memory. The ideal situation is $\tau_r >> \tau_f$, for which the molecule is stationary while it radiates its fluorescence. Usually, $\tau_r \approx \tau_f$, for which some reorientation of the molecule occurs during fluorescence radiation.

If a resin undergoes extensional flow in the z direction, then dependence on ϕ can be eliminated because of the axial symmetry of the flow. During processing, resins are subjected to both shear and extensional stresses, but it is the extensional stress which imparts molecular orientation most efficiently. Under extensional flow, assuming axial symmetry, fluorescence anisotropy r is given as $$r_{cw} = r(\infty) + [r(0) - r(\infty)]\left(\frac{\tau_f}{\tau_r} + 1\right)^{-1} \tag{3}$$

where $$r(0) = \frac{[2\langle P_2^2\rangle + \langle P_2\rangle]P_2(\cos\delta)}{2\langle P_2\rangle + 1} \tag{4}$$

and $$r(\infty) = \langle P_2\rangle P_2(\cos\delta) \tag{5}$$

where $P_2$ is the second Legendre orientation term, $$P_2(\cos\theta) = \frac{3\cos^2\theta - 1}{2} \tag{6}$$

and δ is a molecular constant, the angle between the absorption and emission vectors of the dye. The subscript cw refers to the anisotropy measurements obtained using continuous illumination.

Stress induced molecular orientation can be described by a spatial orientation function, f(θ,ϕ), which depends upon the magnitude of the stress and the rate at which it is applied. The relationship between the average orientation cosine factors and f(θ,ϕ) is given by $$\langle\cos^2\theta\rangle = \frac{\int\int \cos^2\theta f(\theta, \phi)\sin\theta d\theta d\phi}{\int\int f(\theta, \phi)\sin\theta d\theta d\phi} \tag{7}$$

In nearly all cases, f(θ,ϕ) is not known. The anisotropy measurement provides information about the second moment.

Another approach to utilizing anisotropy measurements is strictly empirical. In this case, anisotropy observations are used to establish correlations between important materials properties or processing parameters. These correlations are then available for monitoring materials properties. An example of this approach is the method of Bur et al (U.S. Pat. No. 5,151,748, whose disclosure is hereby incorporated by reference in its entirety into this disclosure) in which a correlation between viscosity and fluorescence anisotropy is acquired as a calibration function, and in subsequent observations, the viscosity of a flowing resin is determined by measuring its anisotropy.

Fluorescence has been used in several laboratory studies to measure molecular orientation in solid polymer films and fibers. These studies did not involve sensor development for real-time monitoring of processing, but were focused on measurement science and the fundamental science of fluorescence anisotropy.

Previous optical sensor development for polymer processing has involved sensors for imaging the process stream and for obtaining color attributes of pigmented plastics. Some such sensors have optical fibers to be used in ½-inch bolt sensor ports, but lack polarizing components for obtaining anisotropy measurements.

According to equation (1), the measurement of anisotropy involves the separate observations of $I_{vv}$ and $I_{vh}$. In most commercial fluorometers, the measurement is carried out by mechanically switching the analyzing polarizer from vertical to horizontal. If the process being observed changes faster than the time duration of switching, then useless anisotropy values are obtained.

Other specific examples from the prior art will now be described. The disclosures of the references described are hereby incorporated by reference in their entireties into the present disclosure.

The use of fluorescence measurements is the subject of U.S. Pat. No. 4,521,111 to C. M. Paulson and M. E. Faulhaber. Their technique consists of monitoring fluorescence intensity as the excitation polarizer is continuously rotated. When the direction of excitation light is coincident with the orientation of the absorption dipole of the fluorescent molecule, then maximum fluorescence intensity is observed. When examining an oriented material by this technique, a sinusoidally alternating fluorescence intensity is generated. The method yields a direction of orientation but does not give values of fluorescence anisotropy and moments of the orientation distribution. Also, the sensor design is not suited for insertion into the ½-inch instrumentation ports on many processing machines.

In another application of fluorescence, U.S. Pat. No. 4,651,011 to J. A. Ors and S. F. Scarlata, fluorescence anisotropy is used to monitor the extent of curing of an epoxy material. The technique uses the fact that fluorescence anisotropy is sensitive to rotational relaxation time of the fluorescent molecule being examined. The apparatus uses two photomultipliers to detect $I_{vv}$ and $I_{vh}$, thus requiring a balancing of both detector circuits so that accurate anisotropy values can be obtained. Also, the sensor is not designed for use in ½-inch instrumentation ports.

Fluorescence was also the subject of U.S. Pat. No. 5,037,763 to J. R. Petisce who employed fluorescence to monitor epoxy curing using temperature and viscosity sensitive fluorescent dye molecules. Fluorescence anisotropy is not measured by the apparatus of Petisce et al, nor is a sensor design presented for ½-inch bolt size.

Optical sensors of the ½-inch bolt design are the subjects of U.S. Pat. No. 4,529,306 to L. B. Kilham and D. W. Riley and U.S. Pat. No. 5,369,483 to P. E. Wilson. The sensor of Kilham and Riley contain focusing lenses and an optical fiber for the purpose of obtaining images of a process stream. Wilson's sensor contains optical fibers for the transmission of light to a spectrophotometer for the purpose of analyzing the color of a pigmented polymer. There are no polarization elements in either sensor, so that fluorescence anisotropy measurements can not be made with these devices.

Furthermore, two U.S. patents based on fluorescence measurements have been issued for developments in the laboratories of the present inventors, U.S. Pat. No. 5,151,748 (1992) to A. J. Bur, R. E. Lowry, S. C. Roth, C. L. Thomas and F. W. Wang, and U.S. Pat. No. 5,384,079 (1995) to A. J. Bur, F. W. Wang, C. L. Thomas, and J. L. Rose. Although a design drawing is shown in the '748 patent document, this patent is a measurement method patent which contains no claims regarding sensor design. The '079 patent was for applications using temperature and viscosity sensitive fluorescent dyes to detect thermodynamic phase transitions during polymer injection molding; fluorescence anisotropy was not used in this method.

Finally, the concepts described above and other concepts relating to fluorescence measuremet are described in further detail in the following references:

J. H. Nobbs, D. I. Bower and I. M. Ward, *Polymer* 15, 287 (1974);

L. L. Chappoy, D. Spaseska, K. Rasmussen and D. B. DuPre, *Macromolecules* 20, 680 (1979);

B. Erman, J. P. Jarry and L. Monnerie, *Polymer* 28, 727 (1987);

A. J. Bur, R. E. Lowry, C. L. Thomas, S. C. Roth and F. W. Wang, *Macromolecules* 25, 3503 (1992); and A. J. Bur, R. E. Lowry, C. L. Thomas, S. C. Roth and F. W. Wang, *Proc. Ann. Tech. Mtg. Soc. Plastics Eng, May,* 1992, p. 2088.

SUMMARY OF THE INVENTION

It is an object of the invention to provide a sensor which can be used for rapid and simultaneous acquisition of $I_{vv}$ and $I_{vh}$ at temperatures customary for polymer processing, up to 300° C.

It is a further object of the invention to provide a sensor probe head for one-sided sensing.

It is a further object of the invention to provide a sensor to fit the standard instrumentation port on plastics processing machines.

It is a further object of the invention to provide a sensor probe for real-time measurements of actual process conditions.

To achieve these and other objects, the invention is directed to an optical sensor for sensing a fluorescence anisotropy of a sample, the optical sensor comprising: means for producing linearly polarized light and for causing the linearly polarized light to be incident on the sample; polarizing means for receiving return fluorescence light from the sample and for splitting the return fluorescence light into a first linearly polarized component and a second linearly polarized component, the first and second linearly polarized components having orthogonal directions of polarization; means for detecting amplitudes of the first and second linearly polarized components and producing an output representing the amplitudes of the first and second linearly polarized components; and means, receiving the output, for computing the fluorescence anisotropy in accordance with the output.

The invention is further directed to a method for sensing a fluorescence anisotropy of a sample, the method comprising: (a) producing linearly polarized light and causing the linearly polarized light to be incident on the sample; (b) receiving return fluorescence light from the sample and splitting the return fluorescence light into a first linearly polarized component and a second linearly polarized component, the first and second linearly polarized components having orthogonal directions of polarization; (c) detecting amplitudes of the first and second linearly polarized components and producing an output representing the amplitudes of the first and second linearly polarized components; and (d) computing the fluorescence anisotropy in accordance with the output.

BRIEF DESCRIPTION OF THE DRAWINGS

A preferred embodiment of the invention will now be described in detail with reference to the drawings, in which:

FIG. 3C shows an expanded view of a portion of the sensor of FIGS. 3A and 3B and also shows the light paths of vertical and horizontal polarizations of the fluorescence through this portion of the sensor;

FIG. 7 shows a slit-die rheometer containing a one-inch-square port for the sensor of FIGS. 3A–3C;

DETAILED DESCRIPTION OF THE PREFERRED EMBODIMENT

Two designs of the sensor head are shown in FIGS. 3A–3C and FIG. 4.

Figure 3A:
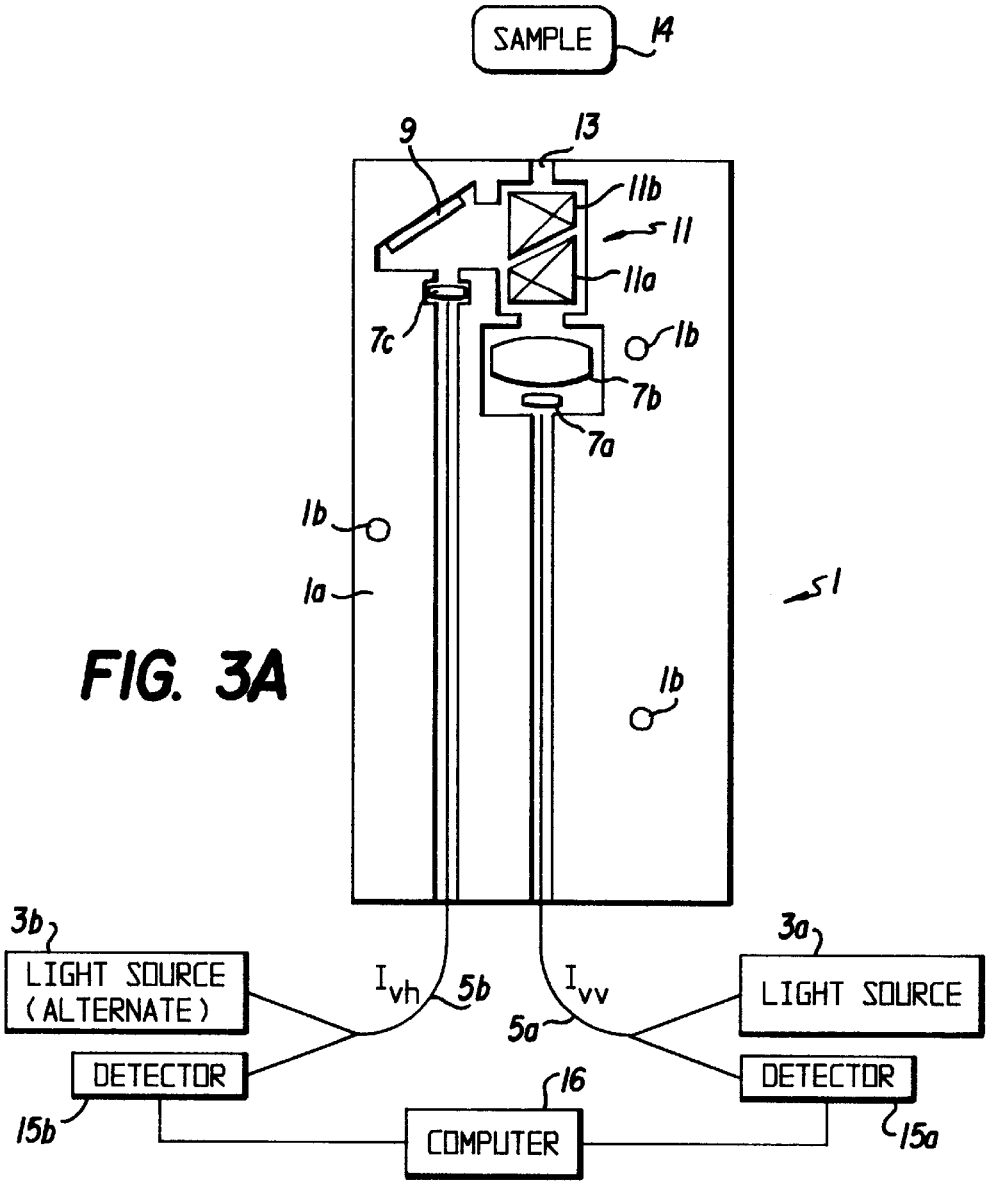
FIGS. 3A and 3B show a side view and a head-on view, respectively, of a square-head sensor according to a preferred embodiment of the invention.
Figure 3B:
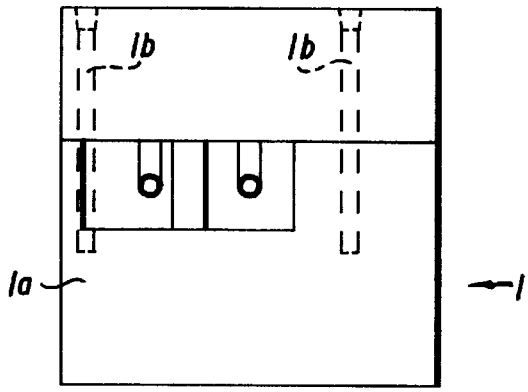

A sensor head 1 having a body 1*a* with square cross section, as shown in FIGS. 3A–3C, is employed in order to maintain a fixed and recognizable direction of the light polarization. The body can be held in place with screws 1*b*.

Excitation light is produced by a suitable light source 3*a* or 3*b*, such as a laser, xenon arc lamp or halogen lamp, and enters the sensor head through optical fiber bundle 5*a* or 5*b*, whose structure will be explained below. Light exiting this sensor is applied via lenses 7*a*, 7*b* or via lens 7*c* and mirror 9 to polarizer 11, such as a Glan-Taylor polarizer, which polarizes the light to have a polarization direction parallel to a side of the square. The sensor fits into a corresponding square receptacle, or it is mounted with screws 1*b* with a fixed orientation directly above the material being examined.

The square sensor head 1 contains a Glan-Taylor polarizer 11 having two calcite crystals 11*a*, 11*b* separated by a fixed air space of approximately 0.1 mm. Both $I_{vv}$ and $I_{vh}$ were obtained from this arrangement. Excitation light from light source 3*a* is transmitted by the optical fiber bundle 5*a* in the central channel of the sensor and becomes vertically polarized by the calcite polarizer 11. The vertically polarized light is made incident on a sample 14 through aperture 13 in the sensor tip.

The resultant fluorescence from the sample 14 enters the sensor head through aperture 13 and is analyzed horizontally and vertically by the same calcite polarizer 11. Because of its birefringence, the calcite polarizer 11 separates the fluorescence into horizontally and vertically polarized components. The horizontal polarization reflects off the interface between the two crystals 11*a*, 11*b* to the mirror 9 and the lens 7*c* and therefrom and into the optical fiber bundle 5*b* of the left channel, which collects it for transmission to the detector 15*b*. The vertical component of fluorescence is transmitted straight through the polarizer 11 to the optical fiber 5*a* in the central channel and then transmitted to the detector 15*a*. The outputs of detectors 15*a* and 15*b* are supplied to computer 16, which can be any appropriate computing device, for computation of the anisotropy in accordance with the theory set forth above.

The light beam transmission paths of $I_{vv}$ and $I_{vh}$ through the sensor are shown in FIG. 3C. When it is desired to detect $I_{hv}$ and $I_{hh}$, as will be described below, alternate light source 3*b* can be used instead of light source 3*a*.

Figure 4:
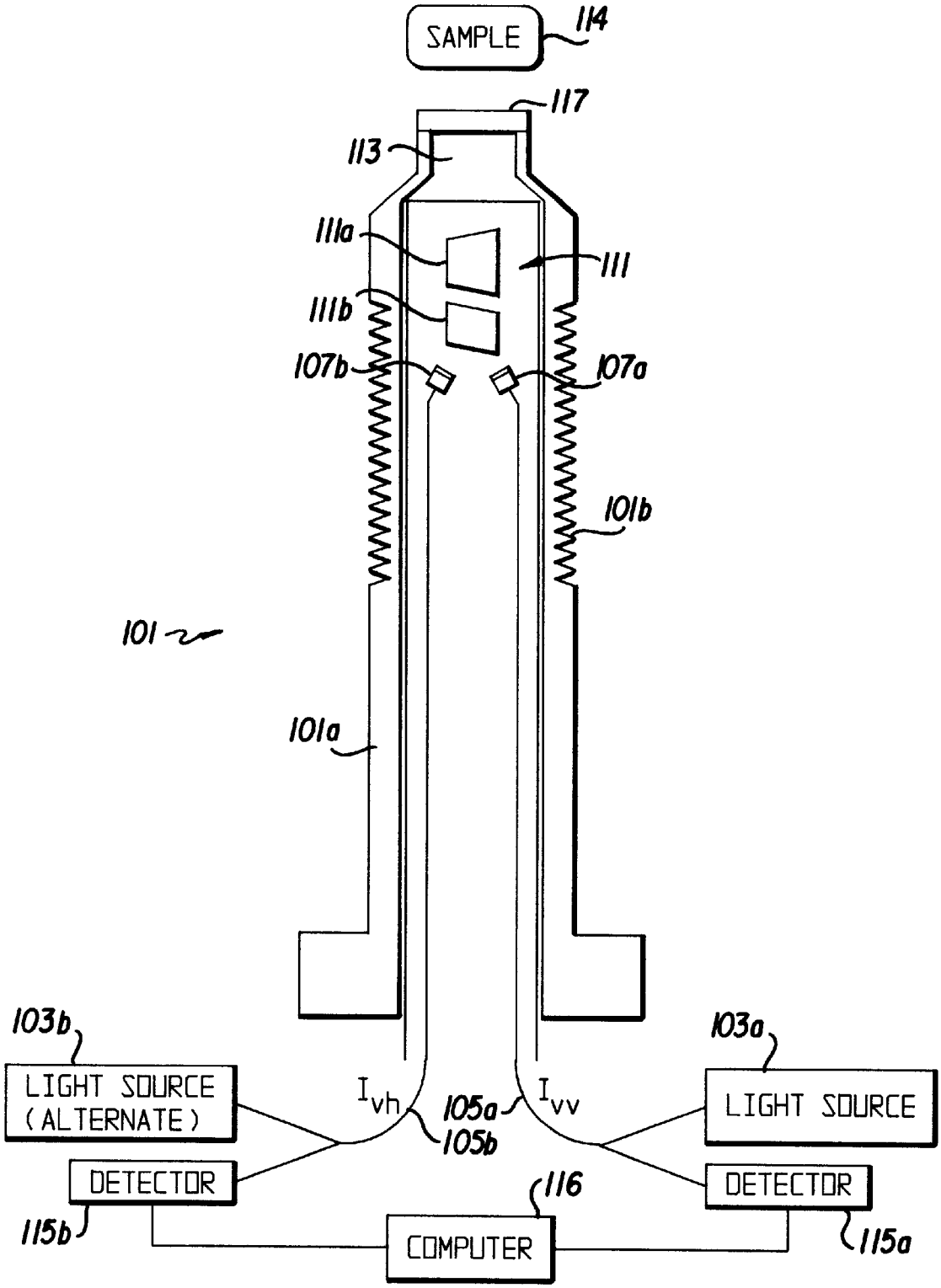
FIG. 4 shows a sensor design for use in a ½-inch bolt.

The sensor 101 shown in FIG. 4 is designated as the bolt sensor and has a body 101*a* which is designed for insertion into the standard ½" diameter instrumentation port which exists on many processing machines, where it is held in place with threading 101*b*. The direction of the polarized light is controlled by orienting the insert containing the polarizer 111 (for example, a Glan-Taylor or Wollaston polarizer). Except as set forth below, sensors 1 and 101 operate in essentially similar fashions.

The ½-inch bolt sensor head 101 uses a Wollaston type calcite crystal polarizer 111. Like Glan-Taylor polarizer 11, polarizer 111 includes two crystals 111*a*, 111*b* separated by an air space. In this case, excitation light from source 103*a* is transmitted by the fiber 105*a* and lens 107*a* and is vertically polarized. The vertically polarized light exits the sensor head through aperture 113 and sapphire window 117 and is made incident on the sample 114.

The vertical and horizontal components of fluorescence light from the sample 114 exit the polarizer 111 in beams at a fixed angle of divergence. The optical fiber bundles 105*a*, 105*b* and lenses 107*a*, 107*b* are set with the appropriate angles of address to the crystal in order to collect $I_{vv}$ and $I_{vh}$.

Sensor 101 can have light sources 103*a*, 103*b* and detectors 115*a*, 115*b*, like light sources 3*a*, 3*b* and detectors 15*a*, 15*b* of sensor 1. Alternatively, sensor 101 can have detector 215 shown in FIG. 5A.

Optical fibers 5*a* and 5*b* of sensor 1 and optical fibers 105*a* and 105*b* of sensor 101 have different transmission factors. In addition, the light paths for $I_{vv}$ and $I_{vh}$ contain different optical elements. The result is different transmission factors for the intensities $I_{vv}$ and $I_{vh}$. In order to compensate for these differences, it is common practice to determine the G factor for the sensor. The G factor is obtained by calibrating the sensor using a sample of known anisotropy. If r is known, then G can be obtained from $$r = \frac{I_{vv} - GI_{vh}}{I_{vv} + 2GI_{vh}} \tag{8}$$

where $I_{vv}$ and $I_{vh}$ are the measured light intensities and G is a sensor constant which compensates for the differences in transmission factors for $I_{vv}$ and $I_{v/r}$ Equation (8) becomes the working equation for calculating r from the measured light intensities.

In detector 215, the two light signals $I_{vv}$ and $I_{vh}$ from fiber bundles 105*a*, 105*b* are alternately detected by the same photomultiplier tube (PMT) 221 using the chopper 223 and filter 225. The signals are then separated by using a gated photon counter 227 and stored in the computer. The reason for using this detector arrangement is that the two signals are detected by the same PMT and photon counter, thus avoiding problems associated with different amplification factors and drift in those factors for two detection circuits.

Light transmitted to the PMT usually contains a component representing the intensity of the excitation wavelength due to reflection of excitation light from the lens 107*a* or 107*b* in the sensor head. This is filtered out using cut-on and/or bandpass filters 225.

The rate of chopper rotation is determined by the rate of change occurring in the material under investigation. For most resin processing, 3000 revolutions per minute, the speed used for the measurements presented below, is sufficiently fast.

Whichever detecting arrangement is used, computer 116, which can be any appropriate computing device, receives the output and computes the anisotropy in accordance with the theory set forth above.

Figure 5B:
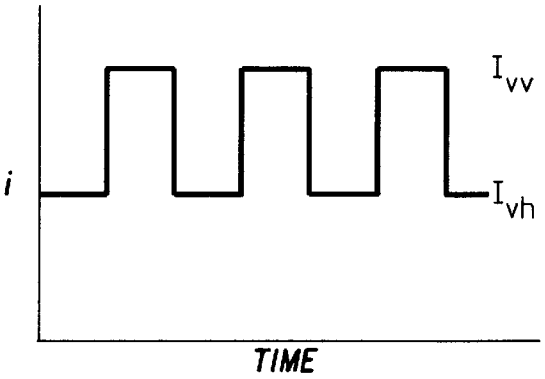
FIG. 5B shows an output of the detection arrangement of FIG. 5A.
Figure 5A:
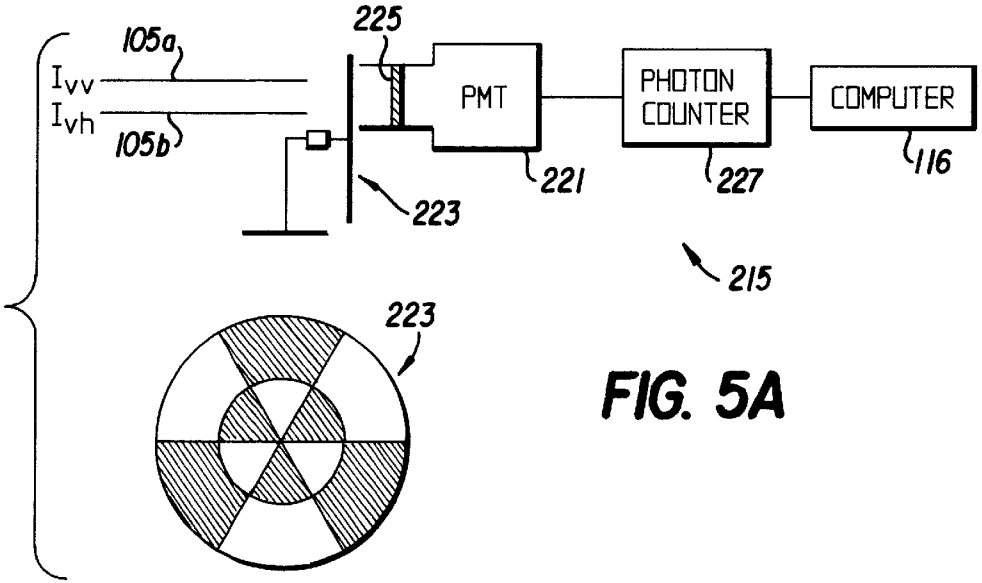
FIG. 5A shows a detection arrangement for the vertical and horizontal components of fluorescence using a chopper.

FIG. 5B shows an output of the detector 215 of FIG. 5 as a function of time. Detected intensity i alternates between $I_{vv}$ and $I_{vh}$.

Figure 1:
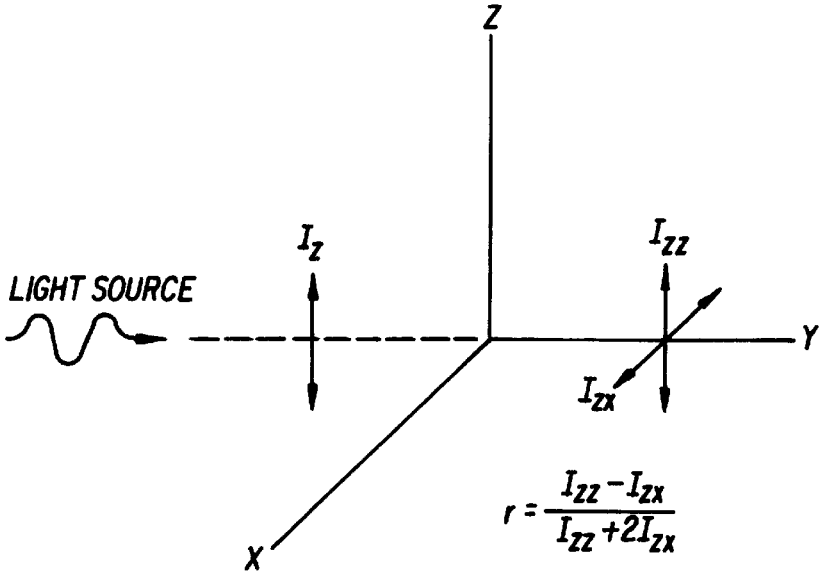
FIG. 1 shows a rectangular coordinate system used in the definitions of polarized light orientations and fluorescence anisotropy.
Figure 2:
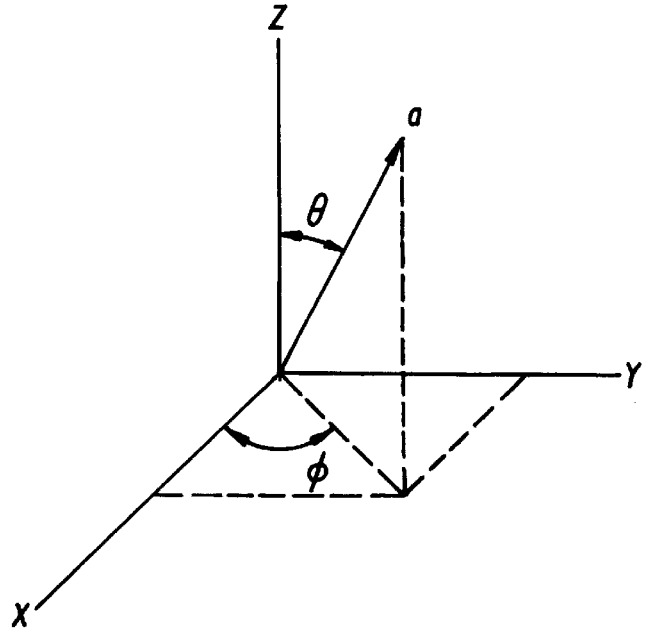
FIG. 2 shows a spherical coordinate system used in expressing the orientation of a molecular absorption dipole.
Figure 6:
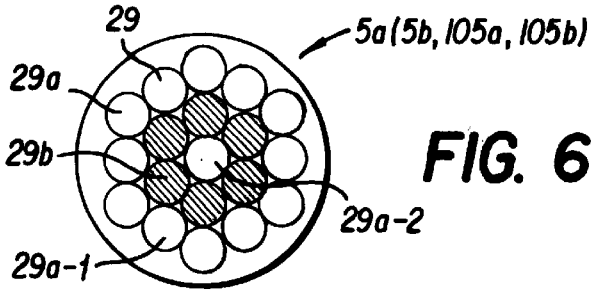
FIG. 6 shows a cross section of a fiber bundle used in the sensor of FIGS. 3A–3C or in the sensor of FIG. 4.

A cross-sectional view of fiber bundle 5*a*, 5*b*, 105*a* or 105*b* is shown in FIG. 6. Each bundle contains nineteen fibers 29 with a 200 $\mu$m diameter core. These fibers 29 include thirteen fibers 29*a* used for collection of the fluorescence and six fibers 29*b* used to transmit the excitation light to the resin. The fiber arrangement in the bundle is in concentric circles. The thirteen fibers 29*a*, namely, twelve fibers 29*a*-1 of the outer circle and the central fiber 29*a*-2, are collection fibers, while the six fibers 29*b* in the second circle are excitation fibers. Upon exiting from the sensor head, the optical fibers are bifurcated into excitation bundles carrying fibers 29*b* and collection bundles carrying fibers 29*a*.

Usually, the bundle of six fibers 29*b* in the fiber bundle 5*b* or 105*b* in the left channel is not used. However, it can be utilized to obtain an alternate anisotropy, r', by transmitting excitation light through it. In this case, $I_{hv}$ and $I_{hh}$ are measured, and r', is derived from the following equation:

$$r' = \frac{GI_{hh} - I_{hv}}{GI_{hh} + 2I_{hv}} \tag{9}$$

The symmetry of the orientation can be examined from r and r'.

The sensor designs of FIGS. 3A–3C and 4 are an improvement in several respects over the design presented by Bur et al in 1992 (U.S. Pat. No. 5,151,748). Using the '748 sensor head, the components $I_{vv}$ and $I^{vh}$ are not measured simultaneously, but are obtained one at a time by switching back and forth from one polarization to the other. The '748 sensor has only one fiber for the excitation, which limits the intensity of generated fluorescence. Also, the '748 sensor was not designed for high-temperature operation.

Figure 8:
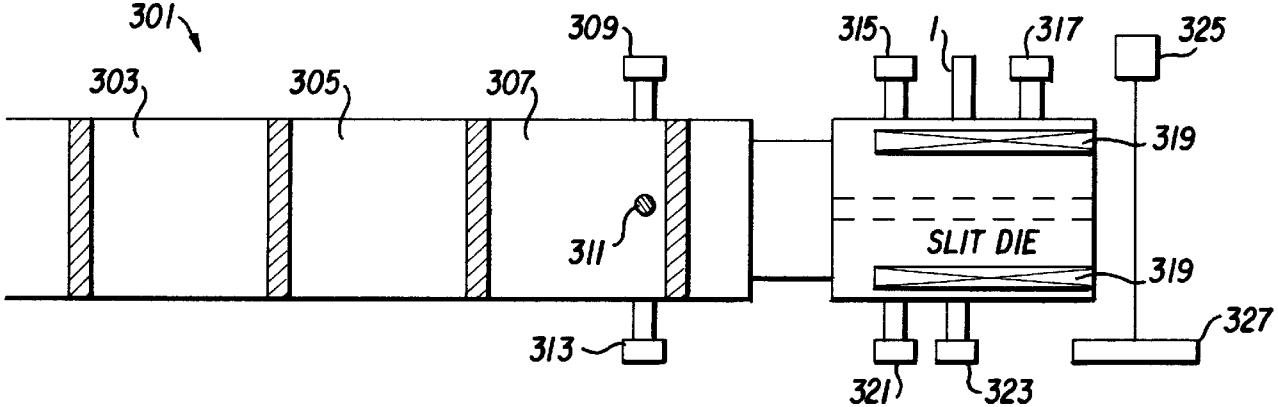
FIG. 8 shows the slit-die rheometer of FIG. 7 attached to an extruder.

One use of sensor head I is shown in FIGS. 7 and 8. FIG. 7 shows a slit-die rheometer 31 having a 2 mm slit 33. The rheometer 31 also has six instrumentation ports for pressure, temperature, and optical sensors, namely, one 1 " square port 35 or receiving sensor head 1 and five standard ½-inch ports 37.

As shown in FIG. 8, during processing, the rheometer 31 is attached to the exit end of extruder 301, whose basic structure and functionality are familiar to those skilled in the art of resin extrusion. Extruder 301 includes heater zones 303, 305 and 307, infrared radiometer 309, optical fiber 311 and thermocouple/pressure transducer 313. Rheometer 31 is heated by cartridge heaters 319 and is equipped with pressure transducers 315, 317 spaced 50.8 mm, thermocouple 321 and optical fiber 323 as well as sensor head 1. The pressure transducers 315 and 317 allow measurement of an in-line pressure drop of a flowing resin. Measurements of fluorescence anisotropy have been carried out as a function of pressure drop (shear stress) during resin extrusion through the dye. At the exit end of rheometer 31 are load cell 325 and weighing pan 327.

Demonstration of the sensor operation was performed using several polymer/fluorescent dye combinations, namely, polyethylene doped with perylene and bis(di-tert-butylphenyl)perylenedicaboximide (BTBP), polybutadiene doped with diphenyl hexatriene (DPH), and cross-linked polybutadiene rubber doped with DPH. One factor considered in choosing these dyes is their geometrical asymmetry because it is desired to study molecular orientation under shear and extension stress fields.

The structures of BTBP, perylene and DPH are shown as Formulae I, II and III, respectively. The arrow in Formula III indicates the absorption dipole of DPH.

(I)

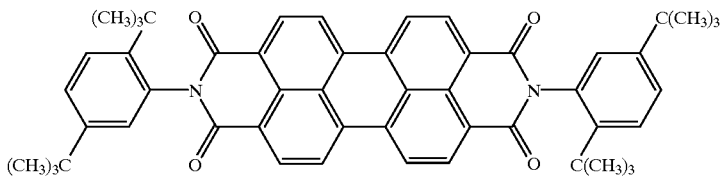

Bis(-di-tert-butylphenyl)-perylenedicarboximide

-continued (II)

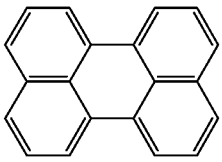

Perylene (III)

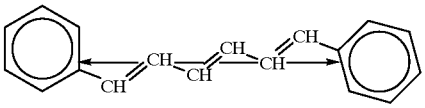

Diphenyl Hexatriene

Figure 9A:
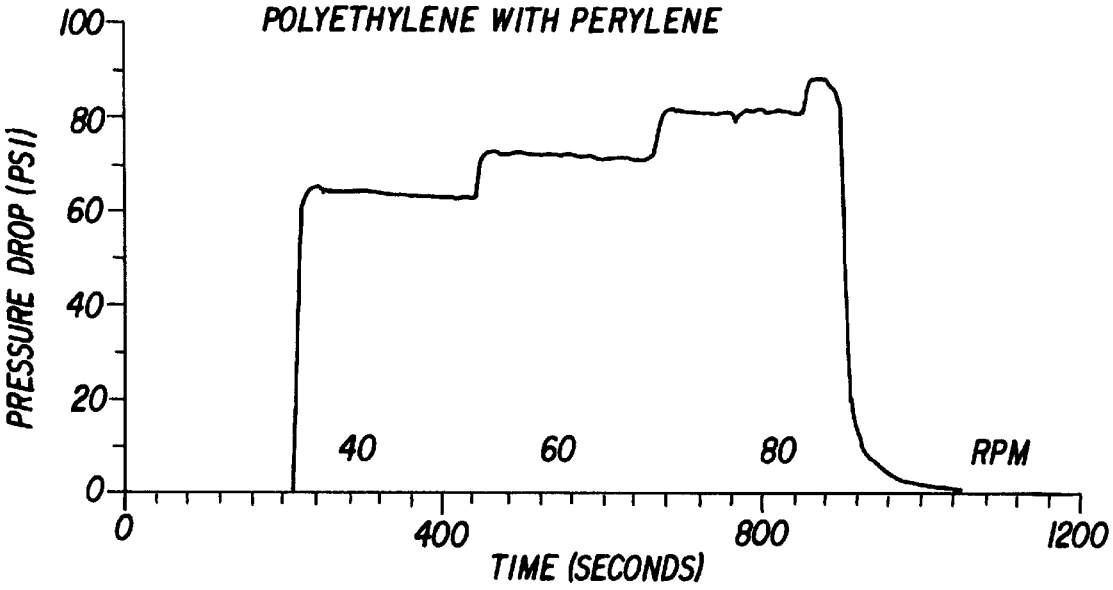
FIG. 9A shows a plot of pressure drop in a slit die as a function of time for polyethylene doped with perylene.
Figure 9B:
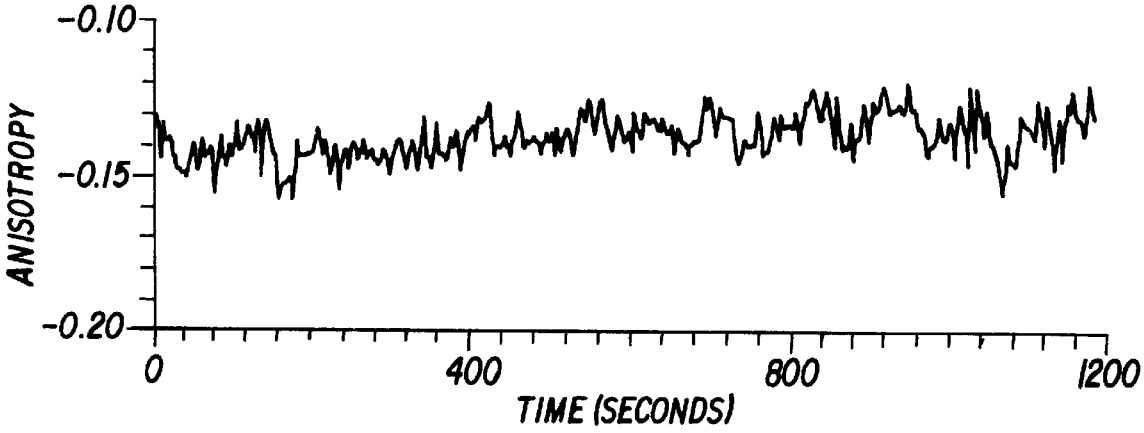
FIG. 9B shows a plot of fluorescence anisotropy in a slit die as a function of time for polyethylene doped with perylene.
Figure 10A:
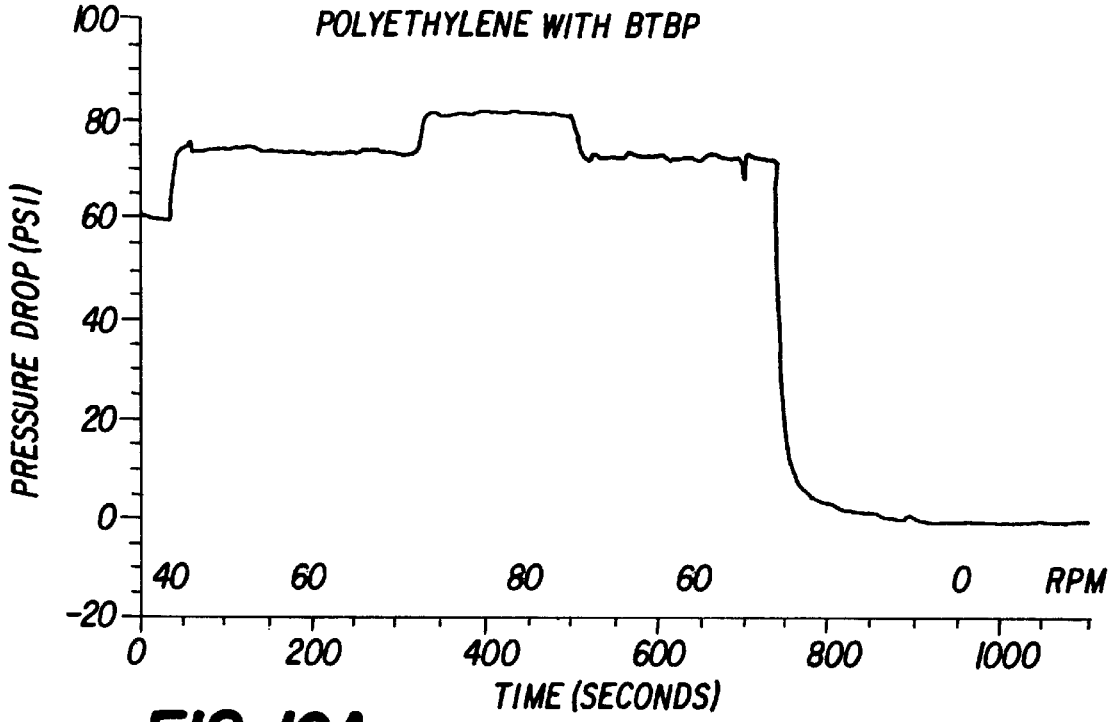
FIG. 10A shows a plot of pressure drop in a slit die as a function of time for polyethylene doped with BTBP.
Figure 10B:
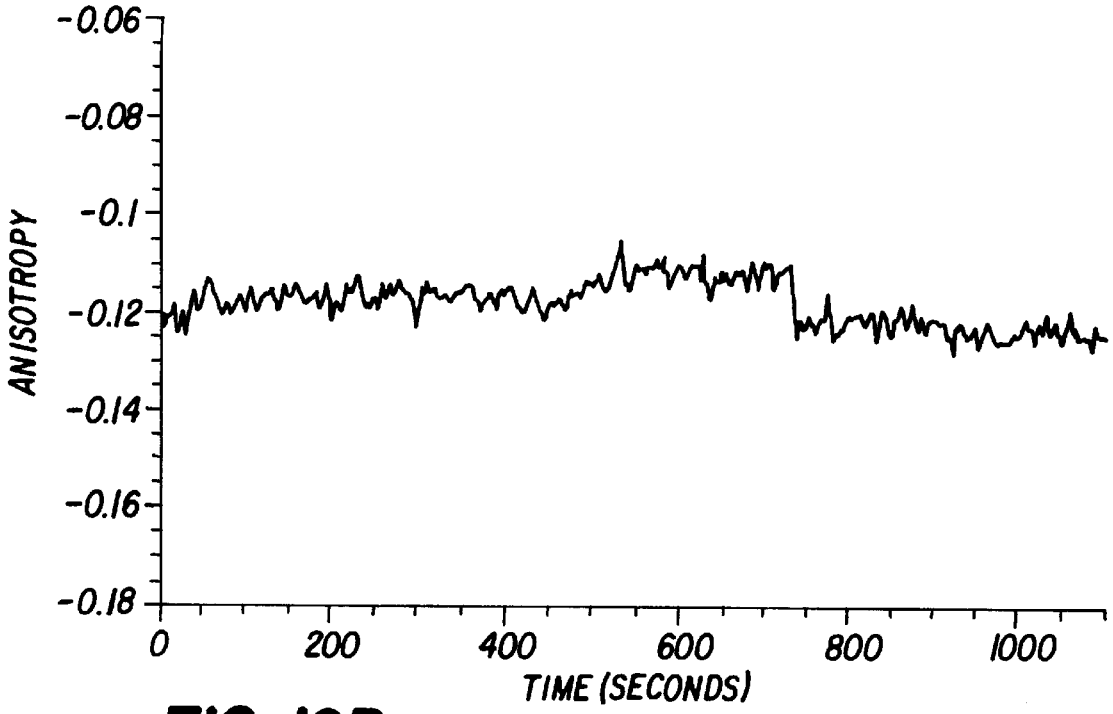
FIG. 10B shows a plot of fluorescence anisotropy in a slit die as a function of time for polyethylene doped with BTBP.

In FIGS. 9A and 9B, pressure drop and anisotropy, respectively, in the slit die are plotted as functions of time for extrusion of polyethylene doped with perylene. For these data, the square sensor head was located in the slit die maintained at 160° C.; the arrangement is shown in FIGS. 7 and 8 and described above. Measurements were made while increasing the screw rpm from 0 to 80 and return to 0. The pressure drop is proportional to the shear stress applied to the flowing resin which, for this extrusion, took place at a strain rates which varied from 10 to 50 $s^{-1}$. It was observed that anisotropy stayed relatively constant as screw rpm was increased and decreased. Small changes that do occur in the data of FIGS. 9A and 9B appear to be the result of the pressure dependence of $\tau_r$. A similar result, shown in FIGS. 10A and 10B, was obtained for extrusion of polyethylene doped with BTBP.

It is believed that the perylene molecule is not oriented by shear stress applied to the resin during extrusion. It is further believed that the dye molecule occupies free volume cells and has interaction with the host resin that is restricted to the local micro-environment. Shearing stresses cause orientation at macromolecular dimensions associated with intermolecular entanglements while the micro-molecular neighborhoods remain relatively undisturbed. Other anisotropy measurements have shown that, if the fluorescent dye molecule is covalently bonded to the polymer molecular chain, then anisotropy becomes sensitive to shear stress because the fluorescent moiety is able to participate in the macromolecular orientation of the entangled network.

Although the results of FIGS. 9A, 9B, 10A and 10B show that anisotropy of a free dye is insensitive to shear stress, such is not the situation for extensional stress. The distinction between extensional flow and shear flow is defined in terms of the strain rate or velocity gradient in the flowing resin. During shear flow, the velocity gradient is perpendicular to the direction of flow. During extensional flow, the velocity gradient is parallel with the direction of flow. Resin flow during processing is often a combination of shear and extensional flows. Being able to detect the presence of extensional flow in a predominately shear flow process is a usefull capability because the behavior of the final product depends on the stresses applied to it during processing. Extensional stress is of special interest to processors because it causes substantial molecular orientation relative to that caused by shear stress of the same magnitude.

Anisotropy of a free dye is shown to be sensitive to extensional stress in two experiments using the square sensor head 1: (a) the free dye is doped into cross-linked polybutadiene; and (b) the free dye is doped into the polybutadiene melt. For cross-linked polybutadiene rubber, diphenyl hexatriene (DPH) was doped into resin using a carrier solvent which swelled the polymer. The solvent was evaporated, and the polymer specimen was washed in order to remove any dye from the surface. For the polybutadiene melt, DPH and the polymer were mixed using a common solvent which was subsequently evaporated.

Figure 11:
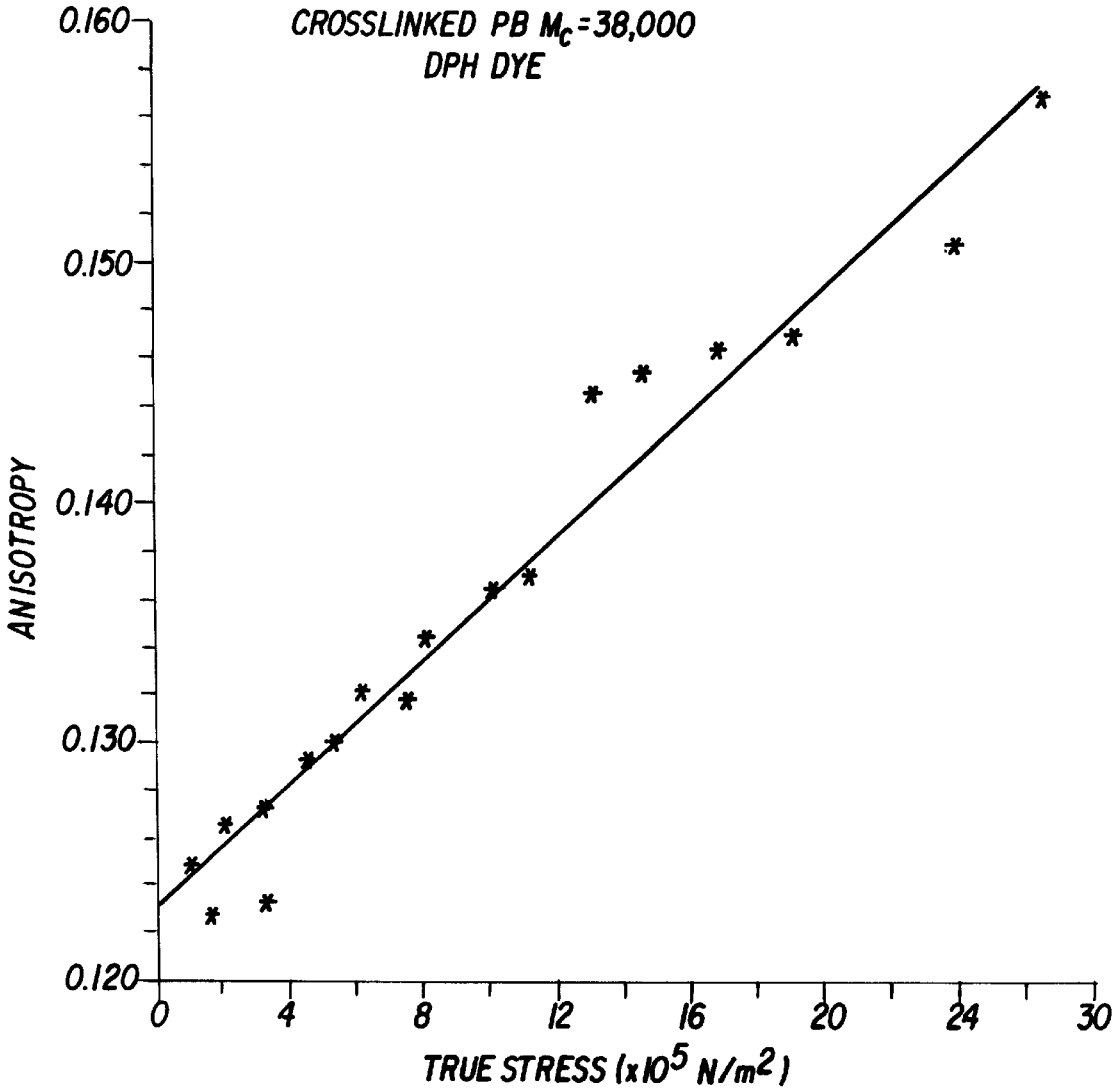
FIG. 11 shows a plot of fluorescence anisotropy as a function of applied stress for cross-linked polybutadiene doped with DPH.

Results of extensional experiments using cross-linked polybutadiene are shown in FIG. 11. In these experiments, the specimen behaved as a rubber and achieved extension of 350% at the highest stress. Anisotropy increases with applied stress and has a linear dependence on stress. Increasing anisotropy means that the DPH absorption dipole (designated by the arrow in FIG. 9C) orients in the direction of extension. The linear relationship between anisotropy and stress indicates that extensional stress imparts orientation to the resin at the micromolecular level.

Figure 12:
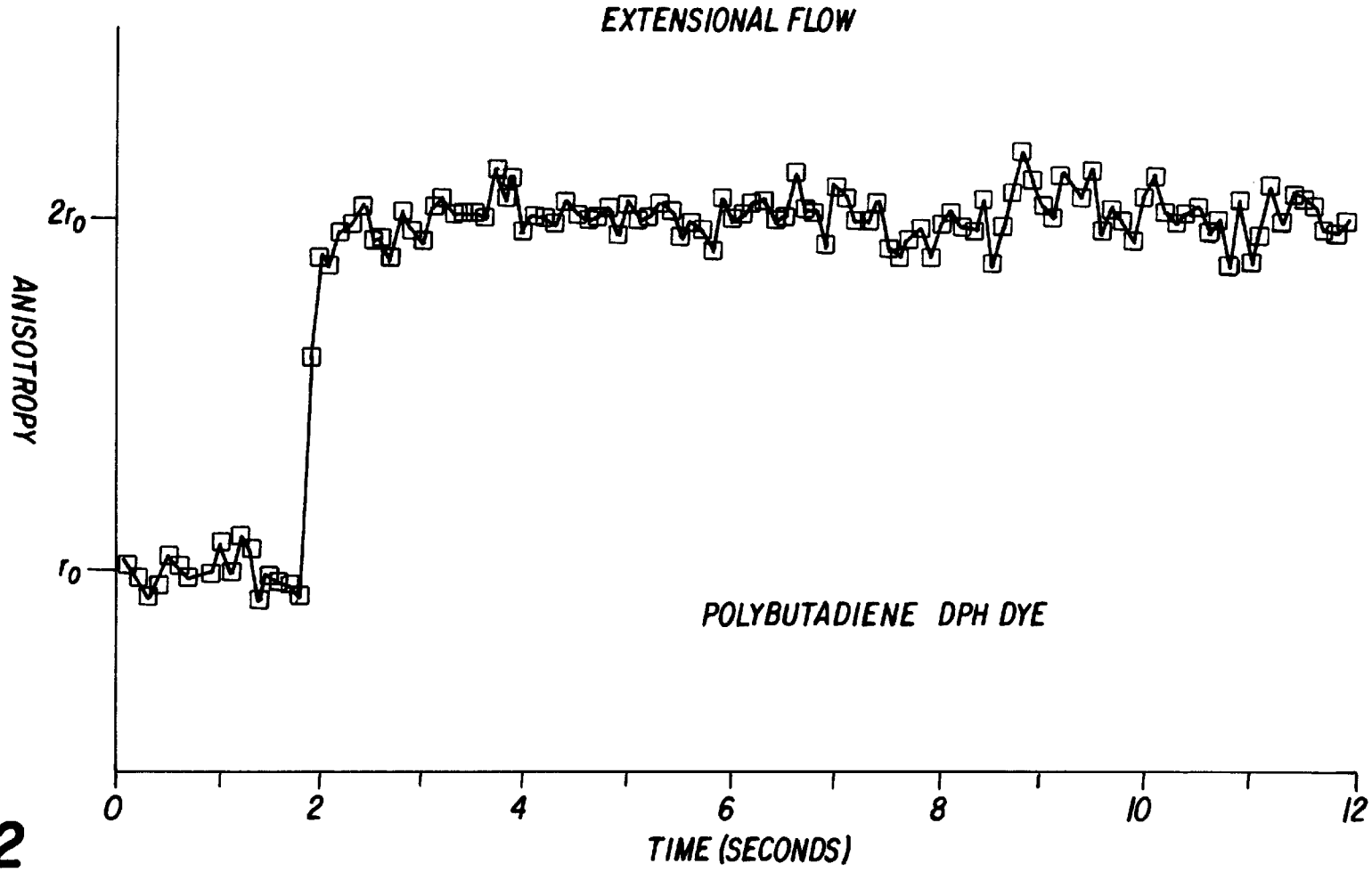
FIG. 12 shows a plot of fluorescence anisotropy as a function of time for polybutadiene melt doped with DPH in which extensional stress is applied at t=2 s.

The extension of the polybutadiene melt was carried out by placing a strip of the melt resin in a mechanical testing machine and pulling it. The results are shown in FIG. 12. Here, anisotropy is plotted versus time during which the melt is extended, starting at rest from time t=2 s. From t=0 to 2 s, no stress was applied to the specimen. At t=2 s, a step function stress was applied, and the polymer flowed at a strain rate of 0.098 $s^{-1}$. For t>2 s, the applied stress was constant while resin flow proceeded uniformly. As with the crosslinked specimen, increasing anisotropy is interpreted as orientation of the DPH absorption dipole in the direction of flow. The fact that the long axis of the DPH molecule is coincident with the direction of the absorption dipole means that under extensional stress this dye molecule orients its long axis in the direction of flow.

The data of FIGS. 9A–12 demonstrate that the anisotropy sensor disclosed herein can be used for real-time monitoring of orientation effects which occur during resin processing and that this sensor can be used at elevated temperatures normally required for polymer processing.

Although a preferred embodiment of the present invention has been set forth in detail above, those skilled in the art will appreciate that other embodiments can be realized within the scope of the invention. For example, modifications disclosed separately can be combined. Therefore, the present invention should be construed as limited only by the appended claims.

We claim:

1. An optical sensor for sensing a fluorescence anisotropy of a sample, the optical sensor comprising:

a source of linearly polarized light and means for causing the linearly polarized light to be incident on the sample in a fixed and recognizable direction of the light polarization;

polarizing means for receiving return fluorescence light from the sample and for splitting the return fluorescence light into a first linearly polarized component and a second linearly polarized component, the first and second linearly polarized components having orthogonal directions of polarization;

means for detecting amplitudes of the first and second linearly polarized components and producing an output representing the amplitudes of the first and second linearly polarized components; and means, receiving the output, for computing the fluorescence anisotropy in accordance with the output.

2. An optical sensor as in claim 1, wherein the means for detecting comprises:

photodetecting means for converting the first and second linearly polarized components into electrical signals;

a first optical fiber means for conveying the first linearly polarized component from the polarizing means to the photodetecting means; and a second optical fiber means for conveying the second linearly polarized component from the polarizing means to the photodetecting means.

3. An optical sensor as in claim 2, wherein the photodetecting means comprises:

a first detector for receiving the first linearly polarized component; and a second detector, provided separately from the first detector, for receiving the second linearly polarized component.

4. An optical sensor as in claim 2, wherein the photodetecting means comprises:

a single photodetector for receiving the first and second linearly polarized components; and a chopper, receiving the first and second linearly polarized components, for allowing only one of the first and second linearly polarized components at a time to be incident on the single photodetector.

5. A method for sensing a fluorescence anisotropy of a sample, the method comprising:

(a) producing linearly polarized light and causing the linearly polarized light to be incident on the sample from a fixed and recognizable direction of light polarization;

(b) receiving return fluorescence light from the sample and splitting the return fluorescence light into a first linearly polarized component and a second linearly polarized component, the first and second linearly polarized components having orthogonal directions of polarization;

(c) detecting amplitudes of the first and second linearly polarized components and producing an output representing the amplitudes of the first and second linearly polarized components; and (d) computing the fluorescence anisotropy in accordance with the output.

6. A method as in claim 5, wherein step (c) is carried out with the following:

photodetecting means for converting the first and second linearly polarized components into electrical signals;

a first optical fiber means for conveying the first linearly polarized component to the photodetecting means; and a second optical fiber means for conveying the second linearly polarized component to the photodetecting means.

7. A method as in claim 6, wherein the photodetecting means comprises:

a first detector for receiving the first linearly polarized component; and a second detector, provided separately from the first detector, for receiving the second linearly polarized component.

8. A method as in claim 6, wherein the photodetecting means comprises:

a single photodetector for receiving the first and second linearly polarized components; and a chopper, receiving the first and second linearly polarized components, for allowing only one of the first and second linearly polarized components at a time to be incident on the single photodetector.

9. The optical sensor of claim 1, wherein the means for causing includes a sensor head having a body with a square cross section.

10. The optical sensor of claim 9, wherein the body with a square cross section fits into a receptacle having a corresponding square shape to receive the square cross section of said body.

11. The optical sensor of claim 1, wherein means for causing includes a sensor head having a body and wherein the body is fixedly mounted so as to cause a fixed orientation of the sensor head relative to a material being examined.

12. The optical sensor of claim 11, wherein the body is fixedly mounted to an istrumentation port of a polymer processing machine.

13. The optical sensor of claim 1, wherein only a single polarizing means is present to create the source of linearly polarized light and to receive the returned fluorescence light.

14. The optical sensor of claim 1, wherein the means for causing comprises six optical fibers of 200 $\mu$m core diameter.

15. The optical sensor of claim 14, including a fiber bundle of 13 optical fibers of 200 $\mu$m core diameter for conveying fluorescence of the sample.

16. The method of claim 5, wherein the linearly polarized light is from two light sources, the polarization of each light source being mutually perpendicular to the other.

* * * * *